United States Patent [19]
Behne et al.

[11] 4,075,761
[45] Feb. 28, 1978

[54] DENTAL HANDPIECE

[75] Inventors: Ernst-August Behne, Bensheim-Auerbach; Reinhard Straihammer, Kirschhausen, both of Germany

[73] Assignee: Siemens Aktiengesellschaft, Berlin & Munich, Germany

[21] Appl. No.: 698,795

[22] Filed: Jun. 22, 1976

[30] Foreign Application Priority Data

Jul. 24, 1975 Germany .............................. 2533189

[51] Int. Cl.² .............................................. A61C 1/10
[52] U.S. Cl. .................................................... 32/27
[58] Field of Search ................................ 32/26, 27, 22

[56] References Cited

U.S. PATENT DOCUMENTS 3,858,323  1/1975  Flatland ................................... 32/27

Primary Examiner—Robert Peshock
Attorney, Agent, or Firm—Hill, Gross, Simpson, Van Santen, Steadman, Chiara & Simpson

[57] ABSTRACT

A dental handpiece provided with a handle having one end connected to a supply hose with several supply lines for liquid or gaseous media. A head section with a dental tool is connected to another end of the handle, and the handle is provided with hollow conductors for carrying the media from the supply lines to the head section. The handle may be rotated about the longitudinal axis of the handle, and relative to the supply hose. The means for rotating the handle is located inside the handle, and the latter is further divided into two portions which are turnable with respect to each other. One of the portions is adjacent to the supply hose, and is non-rotatable with respect to the supply hose. The other portion is connected to the head section and has a length which is at least one-third and at most two-thirds of the overall length of the handle. The part of the handle which is connected to the head section, is in the form of a sleeve-shaped end element which is inserted into a suitably formed mating piece in the other handle portion. The sleeve-shaped element is supported by bearing elements against the respective handle portion.

7 Claims, 4 Drawing Figures

DENTAL HANDPIECE

BACKGROUND OF THE INVENTION

The present invention relates to a dental handpiece with a handle having one end connected to a supply hose. The latter has several supply lines for liquid or gaseous media. At the other end of the handle is located a head section with a dental tool. Hollow conductors are present in the handle for carrying the media from the supply channels to the head section. There is also provided means for achieving rotatability of the handle about its lengthwise axis relative to the supply hose, and for transfer of the media in the area of the parts threaded to one another.

With dental handpieces, to which liquid and/or gaseous media are supplied under pressure, e.g., with turbine handpieces, the handpiece at the instant of connection undergoes a sudden (jerklike) rotary motion which impairs the handling of the handpiece and makes difficult quiet and purposeful operation with the tool mounted on the head section. With a fixed (nonrotary) connection of handpiece and supply hose (mostly a threaded connection) the manipulating ability of the handpiece is severely restricted, particularly with shorter supply hose and higher pressure of the medium.

In order to avoid these disadvantages, it is already known in the art how to provide between the handpiece and the connecting fitting, with which the supply hose is fastened to the handpiece, a separate intermediate piece or element; this intermediate piece permits rotation of the handpiece abouts its lengthwise axis relative to the supply hose. The intermediate piece comprises two bodies of rotation which can be threaded together. With the peripheral surfaces facing one another, these bodies of rotation form annular channels (grooves) for transfer of the media from one body or rotation to the other. The annular channels (grooves) are sealed both against the outside and from each other by O-rings.

Such construction has the disadvantage that the hand-held instrument (handpiece plus intermediate piece) is relatively long and heavy and that the instrument hence becomes cumbersome. Due to the excess length of the instrument, there is exerted on the handpiece — and to an increased extent on the tool mounted in the head section of the handpiece — a pitching moment; to counteract the latter, a more solid grasping of the handle is required. However, the use of the handpiece for an appreciable time interval, such grasping leads to cramps in the fingers which should be avoided. Another disadvantage is that the construction to achieve rotatability of handpiece and supply hose is costly to manufacture.

It is therefore, an object of the present invention to provide a dental handpiece of the foregoing species which has a simpler construction and is hand-held more easily than the known types, and where during usage, no pitching moment with the aforementioned accompanying disadvantages can act on the handpiece.

SUMMARY OF THE INVENTION

The objects of the present invention are achieved by providing that means located inside the handle, divide the latter into two parts which can be threaded together. The portion adjacent to the supply hose (which cannot be turned) is connected to the latter, and the portion connected to the head section has a length which is at least one-third and at most two-thirds of the overall length of the handle.

The arrangement of flexible hollow conductors in accordance with the present invention has the advantage that the danger of leakage in the area of the rotatable parts is to a great extent eliminated. With previously known handpieces of this type, this difficulty is presented by the large number of locations to be sealed; the difficulty is further increased by the fact that the contact pressure of the O-rings must be kept very small in order to ensure easy rotation of the instrument.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
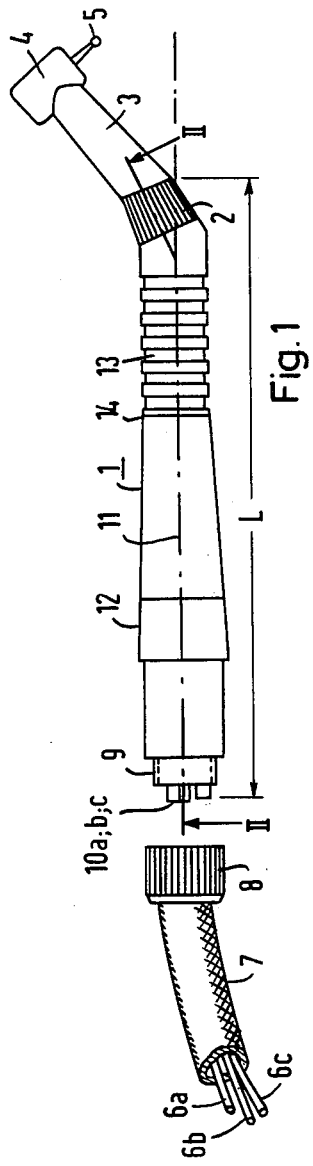
FIG. 1 shows a dental turbine handpiece with part of the associated supply hose.

FIG. 1 shows a dental handpiece with a handle 1 to which a head section 3 is fastened by means of a screw cap 2. The head section 3, at its free end, bears an essentially cylindrical housing 4 in which a compressed-air drive (turbine) for a dental tool 5 is located. To supply the necessary compressed air and the cooling agents that may be necessary for cooling tool 5, there is provided a supply hose 7 which comprises three supply channels 6a through 6c. This hose is fastened by means of a screw cap 8 to a connecting part 9 of the handpiece. The connecting part 9 comprises suitably shaped hose connecting nipples 10a through 10c which, upon sliding the hose 7 onto connecting part 9, are connected to supply channels 6a through 6c.

The handle 1 is subdivided into two parts (portions) 12, 13 (the point dividing the two parts is designated by 14). The second part 13, which is connected to the head section 3, has a length which is at least one-third and at most two-thirds of the overall length L of handle 1. This ensures that the rear section of the handpiece which is the non-rotary first part 12, can be in contact with the hand while the forward section, which is the second part 13 and the head section 3, can be rotated about the lengthwise axis 11 of the handpiece depending on the required manipulating feasibility.

Figure 2:
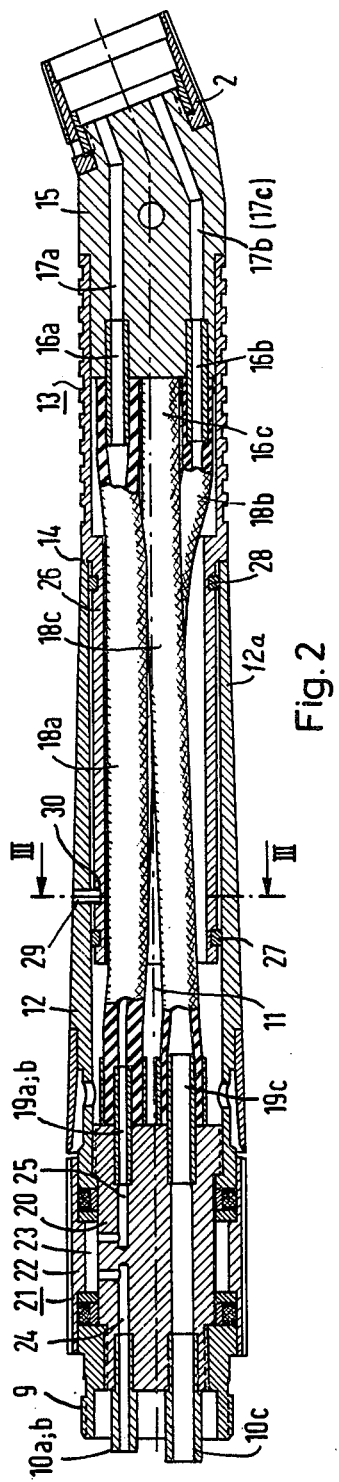
FIG. 2 shows a lengthwise section of the handpiece taken along line II—II of FIG. 1.

FIG. 2 shows the internal design of the handle 1 and shows the arrangement of the means required for screwing the two handle sections or parts together.

The handle section or part 13, which is a tubular or sleeve member, at its forward end, which faces the head section 3, telescopically receives an angle piece 15, which has three connecting links or, nipples 16a through 16c. These nipples are connected, on the one hand, to the channels 17 (a, b, c) leading to the head section 3, and, on the other hand, to flexible hollow conductors or tubes 18a through 18c. The hollow conductors 18 with their other ends are fastened to additional connecting nipples or links 19a through 19c. These are connected, via channels to be described later, to the hose connecting nipples 10. Nipples 10 and 19 are fastened to a valve body 20 to which the nonrotary tubular first part or section 12 of handle 1 is threaded. The valve body 20 is part of a valve 21. By means of this valve the flow of the medium flowing through the lines or channels with the designation a can be controlled. To this end, the valve comprises an actuation ring 22; by means of it, the passage cross-section of valve chamber 23 between the intake channel 24 and the outflow channel 25 can be varied. The actuating ring 22 is located with its center axis at a distance from the center axis 11 and rotatable around this axis, so that, depending on the angular position, a larger or smaller flow cross-section can be adjusted for on the valve. Further details of this valve may be found in German Pat. P. No. 2 207 240.8.

Via the three supply channels 6a through 6c of the supply hose 7, compressed air is supplied for driving the turbine in the head section 3, and cooling air and cooling water are supplied for creating an air-water mixture in the vicinity of tool 5. The compressed air for driving the turbine is carried in the lines with the designation c, the cooling air is carried in lines b and the cooling water is carried in lines a. The quantity of cooling water can be varied by means of valve 21.

Figure 3:
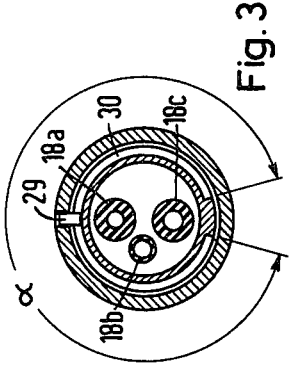
FIG. 3 shows a cross-section taken along line III—III of FIG. 2.

Handle part 13 contains a sleeve-like end portion 26 which protrudes relatively far into the interior of portion 12a of the sleevelike part 12. The end portion 26 is provided with two annular grooves, which are spaced along the axis 11. These hold two slotted bearing rings 27, 28 which constitute the sole support of part 13 on the nonrotary part 12 and provide a bearing between portions 12a and 26 for substantially the entire length of portion 26. The two rings 27, 28 are manufactured from a material commercially known as "Delrin." In place of the rings other low-friction elements (e.g., balls placed in the grooves) may be, of course, provided. Item 29 denotes a pin which is pressed into a suitable drill hole in part 12. The free end of the pin 29 engages an annular groove 30 to provide means for stopping or for limiting the angle of rotation between the parts 12 and 13 to an angle range of between 300° and 350° and, as illustrated in FIG. 3, the groove 30 extends through an angle $\alpha$ of about 335° around the periphery of end portion 26. In addition, pin 29 secures part 13 against axial sliding from portion 12 and against stripping the thread. FIG. 3, which shows a cross-section of the handle taken along line III—III, clearly shows this detent and stopping means.

As illustrated in FIG. 2, the handle 1 has three axial sections or regions which are formed by the parts 12 and 13. The part 12 forms a first section which is tubular and attached to the valve body 20. The part 13 forms a hollow second section terminating in the angle piece 15 and the overlapping tubular portion 12a and sleeve portion 26 form a third section or central region which is a tubular bearing section that interconnects the first and second sections and is a substantial axial portion of the axial length of the handle 1. The flexible tubes 18 which extend from the value body 20 to the angle piece 15 are loosely secured in the tubular or hollow portions of the three sections without any support and allow for relative rotation between the parts 12 and 13.

Figure 4:
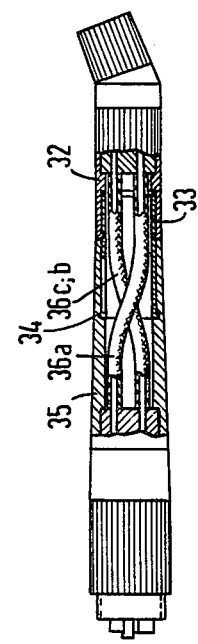
FIG. 4 shows another embodiment of the handpiece in accordance with the present invention.

FIG. 4 shows another embodiment of a handle. In contrast to the above-described embodiment, the portion or second part connected to the rotary part of the handle is not one piece, but comprises two threaded parts 32 and 33. Part 32 which comprises the connecting nipple for the flexible hollow conductors 36 is made of metal; part 33 is a tubular made of synthetic material. The latter is slitted for a major part of its length and at its end, it contains a bead 34 which, after sliding part 33 into the slightly conical handle portion or the first part 35, which is a tubular member with a diameter that increases in the direction toward the connection of the supply hose, detents in a suitably-shaped annular groove. The portion of part 33, which is received in first part 35 coacts with part 35 to form an axially bearing portion, which is hollow to allow passage of the flexible tubes or conductors 36a through 36c through the central axial region and is disposed between the hollow portions of the handle 1. It is evident from the drawing that at least two of the three hollow conductors 36a through 36c are laid crosswise. Thus, a possible disturbing restoring torque can be compensated to a large degree. In order to prevent stripping the threads of the hollow conductors, again — as with the above-described embodiment — stopping means are provided between part 33 and part 35. This stopping means restricts the angle of rotation of the handle 32 to about 335°. The means for rotating the handle in relation to the supply hose are located inside the handpiece, and flexible hollow conductors, solidly connected in the handpiece, are used instead of the O-rings. As a result the disadvantages described earlier in relation to the prior art can be avoided without increasing the length of the handpiece. Since all connections inside the handle are tight, leaks are to a great extent eliminated.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

We claim:

1. In a dental handpiece comprising a handle member which is formed of first and second parts, means interconnecting the two parts for relative rotation therebetween, a supply hose having a plurality of feed channels for a liquid and/or gaseous media being connected to the first part, a head section with a dental tool being connected to the second part, each of the two parts having connecting nipples arranged in the interior thereof, and hollow flexible tubes extending from the nipples of the first part to the nipples of the second part for conveying each of the media from the feed channels of the supply hose to the head section, said means for interconnecting the two parts enabling rotation of the second part of the handle member about a longitudinal axis of the handle member and relative to the supply hose with the flexible tubes compensating for the relative rotation between said two parts, the improvements comprising the second part having a length which amounts to at least one third of the overall length of the handle member, said second part at a free end having a hollow sleeve portion telescopically received in a hollow sleeve portion of the first part, said sleeve portions of the first and second parts forming a bearing disposed in a central axial region of the handle member for supporting the second part and head section for rotation on the first part, and said flexible tubes extending through said central region without support so that the first part is in contact with a hand as the second part and head section are rotated during manipulation of the handpiece.

2. In a dental handpiece according to claim 1, wherein the bearing includes two bearing rings disposed between the hollow sleeve portions of the first and second parts, said bearing rings being positioned adjacent the ends of the hollow sleeve portion of the second part so that the bearing provides support over substantially the entire length of the central axial region.

3. In a dental handpiece according to claim 2, wherein each of the two bearing rings is a slotted ring received in a groove provided at one of said sleeve portions.

4. In a dental handpiece according to claim 2, which includes means extending between the sleeve portions for limiting the angle of rotation of said portions to an angle in a range of between 300° and 350°, said means for limiting preventing axial disassembly of said sleeve portions.

5. In a dental handpiece according to claim 1, wherein said sleeve portion of the second part is fabricated from synthetic material and is provided with a detent member at a free end thereof, said sleeve portion of the first part being provided with a groove for receiving said detent member as the sleeve portion of the second part is slidably received therein so that the coaction of the groove and detent prevents axial disassembly of said first and second parts.

6. In a dental handpiece according to claim 5, wherein the sleeve portion of the second part has longitudinal slots and wherein the interior of the sleeve portion of the first part has a slightly conical construction with a diameter which increases from the free end in the direction toward the supply hose.

7. In a dental handpiece according to claim 1, wherein the first part is attached to a valve means interposed between the first part and the supply hose for regulating fluid flow in one of said flexible tubes.

* * * * *